United States Patent [19]
Pakiam

[11] Patent Number: 4,636,213
[45] Date of Patent: Jan. 13, 1987

[54] IMPLANTABLE PROSTHESIS

[76] Inventor: Anthony I. Pakiam, 3200 University, Des Moines, Iowa 50311

[21] Appl. No.: 694,651

[22] Filed: Jan. 24, 1985

[51] Int. Cl.$^4$ .............................................. A61F 2/12
[52] U.S. Cl. ........................................ 623/8; 128/1 R
[58] Field of Search ...................... 128/92 E, 1 R, 654; 3/1, 36, 1 G; 623/7.8

[56] References Cited

U.S. PATENT DOCUMENTS

| | | | |
|---|---|---|---|
| 3,919,724 | 11/1975 | Sanders | 3/36 |
| 3,922,726 | 12/1975 | Trentani et al. | 128/92 C |
| 4,178,643 | 12/1979 | Cox | 3/36 |
| 4,224,698 | 9/1980 | Hopson | 128/92 C |
| 4,253,201 | 3/1981 | Ross et al. | 3/36 |
| 4,428,364 | 1/1984 | Bartolo | 128/1 R |

FOREIGN PATENT DOCUMENTS

| | | | |
|---|---|---|---|
| 0138006 | 10/1979 | Japan | 3/1.9 |
| 8303193 | 9/1983 | PCT Int'l Appl. | 3/1.9 |

*Primary Examiner*—Richard J. Apley
*Assistant Examiner*—David J. Isabella
*Attorney, Agent, or Firm*—Morton S. Adler

[57] ABSTRACT

A prosthesis for permanent implantation at a selected body location to establish a desired body contour has particular utility and advantages as a mammary implant. It comprises an outer medical grade elastomer closed envelope having a built-in anterior self-sealing valve and an inner like envelope secured to the posterior of the outer envelope and having an anterior injection receiving area with a self-sealing capability secured in a fixed position of registration to the self-sealing valve. A viscous gel is provided intermediate the envelopes for lubrication to minimize or eliminate the incidence of spontaneous rupture. Selected materials are percutaneously injected into or withdrawn from the inner envelope through the registering injection receiving area and the valve with radiopaque indicia associated with the valve to delineate precisely the perimeter of the valve and the precise center thereof for accurate identification from outside the body by means of X-ray or ultrasound whereby the needle can be inserted at an accurate perpendicular attitude to the valve to eliminate the danger of piercing the envelope wall. In a second embodiment, a self-sealing capability is provided only in the valve and in a third embodiment, only a single envelope is used.

10 Claims, 8 Drawing Figures

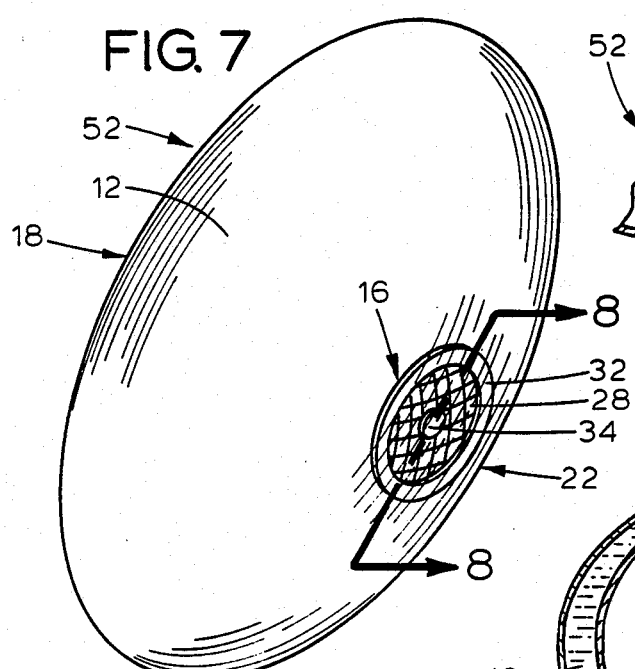
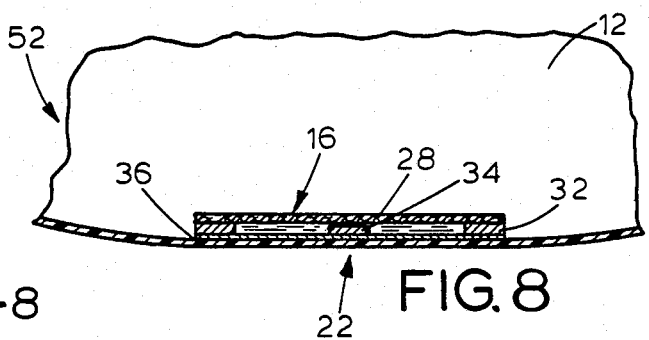
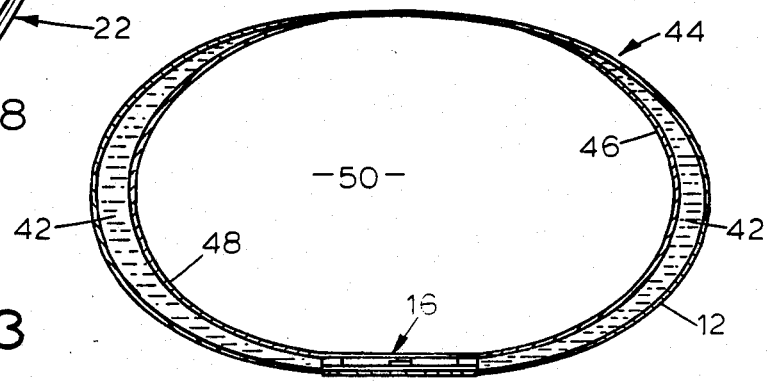
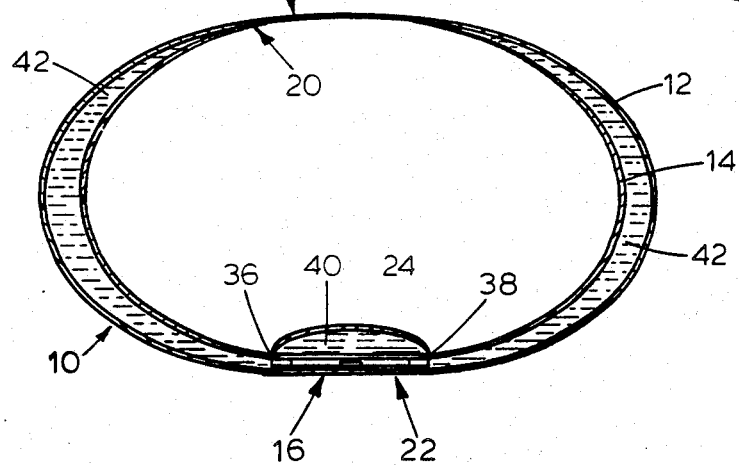

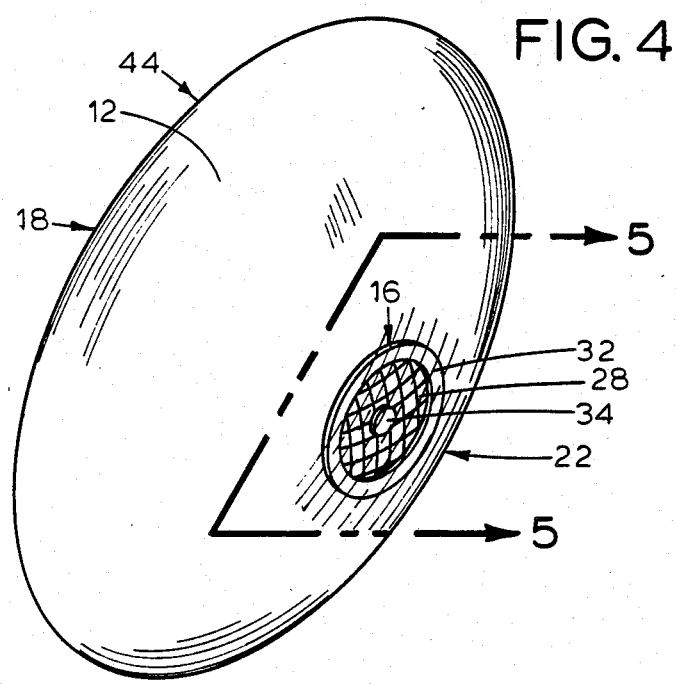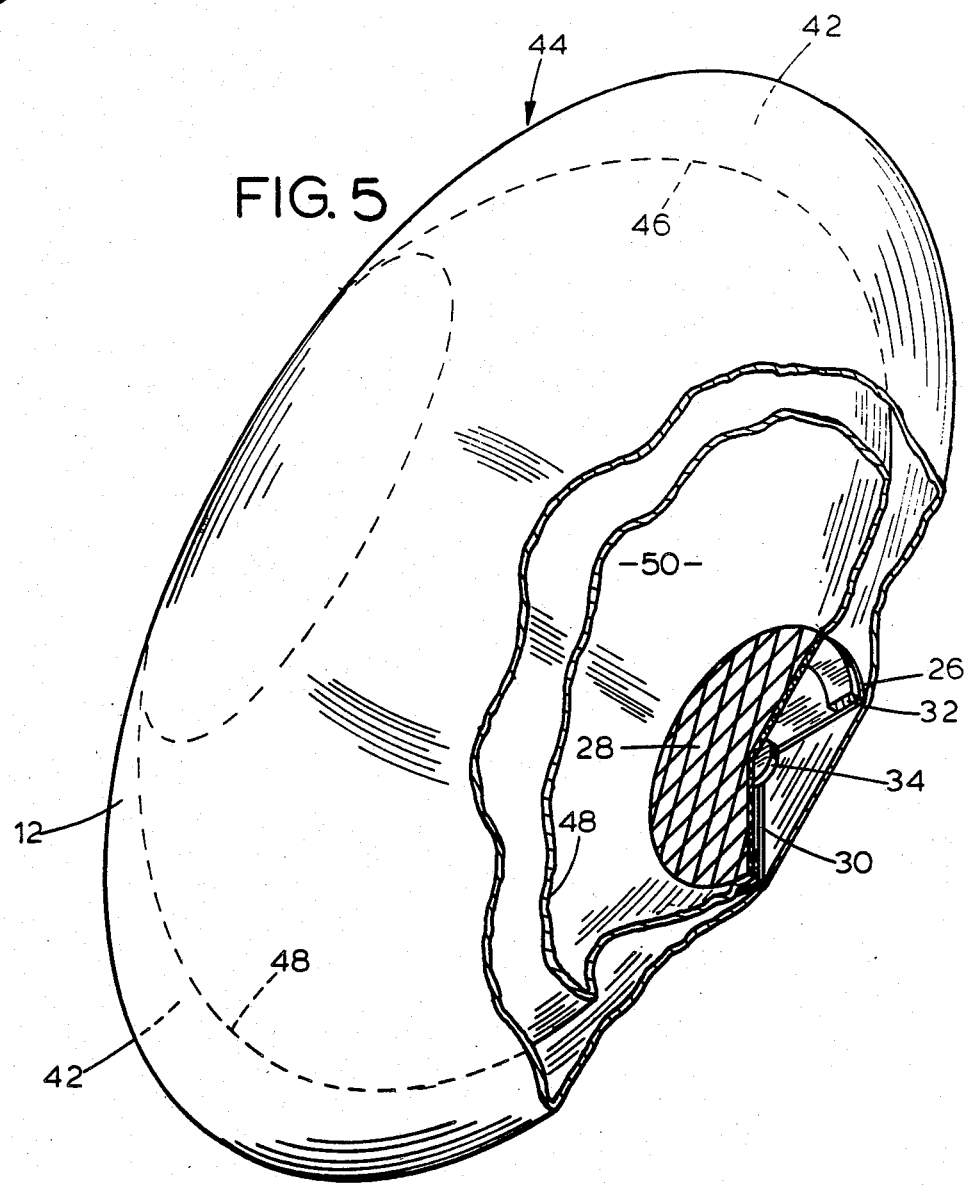

IMPLANTABLE PROSTHESIS

BACKGROUND OF THE INVENTION

This invention relates to improvements in prostheses for permanent implantation to establish a desired body contour and has particular application and advantages in the area of mammary implants.

Throughout the history of our society, the female breast has been a symbol of femininity and an object of sexual stimulation which has been exploited in the arts, in literature and commercially with the result that women who have undergone mastectomies or whose breast structure may be considerably less or greater than might be desired become enmeshed with many physical, emotional and psychological problems. The rehabilitation of such women has been a prime area of interest by the medical profession and particularly plastic surgeons and since the first attempt at breast reconstruction recorded in 1893, considerable progress has been made and documented in that field and in augmentation and reduction mammaplasty.

Two basic procedures have been developed for breast reconstruction. One procedure, which for purposes here can be described generally as the use of skin and muscle flaps in various forms and arrangements, involves the replacement of tight skin and muscles by muscle and skin transfers and transplantation to produce a suitable breast mound. In the other procedure, the lost breast mound is reestablished by implantation of a prefabricated or customed designed prosthesis. Both procedures have well documented advantages and disadvantages related to varying conditions that may be present in any particular patient considering a choice of procedures. It is with the prosthesis procedure that my invention is directed.

This invention will be preferably described in relation to a mammary implant because of its particular advantage for such purpose. Such type of implant is placed in a surgically created body cavity and filled with a saline solution by well known procedures. Postoperatively, the implant may require the serial addition of saline to effect expansion of the skin, withdrawal of fluid to release pressure or reduce the volumetric content, if necessary, or otherwise addition or withdrawal of fluid as may be required as the implant settles into position and swelling diminishes and, at time, the injection or withdrawal of antibiotics and other additives such as steroids may be required as is well known for the study, management and possible control of capsular constracture which is an incidence of implant procedures. Capsular contracture may be described generally as the collection of fibrous or scar tissue that encapsulates the prosthesis and which must be ruptured or broken when it develops. This can be accomplished by a closed capsulotomy which is external manipulation of the breast tissue that is commonly required and relatively simple for some patients with mammary implants but very difficult for others due to a variety of factors so as to require the use of an anesthetic or by an open capsulotomy that involves surgical procedures.

Breast reconstruction, whether by the skin flap or prosthesis procedure involves initial surgical procedures and by its very nature creates emotional, physical and psychological factors for the patient which are inherent with surgery in general and with breast reconstruction in particular so that it is highly desirable to avoid surgery whenever possible in any postoperative treatment. The development of the injectable prosthesis reflects endeavors to provide a method of performing the postoperative procedures indicated by percutaneous injection to avoid surgery but such devices as presently known have certain disadvantages and drawbacks from the standpoint of efficiency and safety that will be pointed out.

The implantable prosthesis procedure was introduced in the mid-seventies in the form of a temporary expandable envelope connected by an elongated tube to an injectable reservoir. The envelope was placed through an incision into the breast cavity and the reservoir was placed in a small subcutaneous pocket posteriorly to the incision. The envelope was supplied from time to time by percutaneous injection into the reservoir, as distinguished from the envelope, to accomplish gradual stretching of the skin to a desired point at which time it was surgically removed and replaced by a permanent implant. The apparent disadvantage and drawback of this early device is the necessity of an undesired second surgical operation. An improvement in this early method has been the replacement of the temporary envelope with a permanent prosthesis but retaining the injectable reservoir which still requires surgery for removal.

A subsequent development to the implant-reservoir procedure has been the prosthesis designed to postoperatively add or withdraw implant additives by percutaneous injection directly into the prosthesis envelope and thus avoid additional surgery such as exemplified by U.S. Pat. Nos. 4,253,201 and 4,428,364. This type of prosthesis includes a self-sealing valve at a selected point on the anterior surface of the prosthesis and is implanted subcutaneously so that the location of the valve for purposes of injection or withdrawal of fluids can be accomplished by palpation by the surgeon. However, such means for locating the valve is dependent upon the subcutaneous location of the prosthesis where palpation is favorable but in the further development of the mammary prostheses art where the placement of the prosthesis is now predominately submuscularly where the incidence of capsular contracture is considerably less, palpation for locating the valve is, for all practical purposes, extremely difficult, if not impossible at time and therefore quite unreliable. A disadvantage of the prostheses where valve location depends upon palpation is that when a capsular contracture occurs, a closed capsulotomy is necessary to make the valve palpable and when inadequate capsule release results from a closed capsulotomy, an open capsulotomy is necessary to expose the valve.

U.S. Pat. No. 3,919,724 discloses a double envelope prosthesis with a self-sealing anterior valve for percutaneous injection directly into the prosthesis through the valve which has an associated pocket filled with a suitable radiopaque material whereby the valve area can be located by X-ray. The inner envelope is secured posteriorly to the outer envelope and is filled by the injection needle passing through both the outer and inner envelope. However, since the inner envelope is collapsible within the outer envelope, there is considerable danger if the prosthesis is deflated of the outer wall being pierced by the needle and causing leakage.

U.S. Pat. No. 4,253,201 addresses the problem of potential damage to the envelope from the injection needle and discloses a single envelope prosthesis with an anterior self-sealing valve for percutaneous injection with the valve being preferably located by palpation. In this device, a cylindrical body extends into the envelope to form a closed chamber for receiving injected material which passes into the envelope through holes in the chamber. One end of the chamber forms a separate pocket with the outside wall about the valve to be filled with a gel mass and it is suggested that radiopaque material can be added to the gel to make it responsive to X-ray. This device does not permit direct injection into the prosthesis but only into a separately constructed inner chamber which adds to the cost of manufacture.

It will be appreciated from the foregoing that the use of the injectable implant presents the ever present danger of damage to the prosthesis envelope by the injection needle that could render the prosthesis useless and require replacement by surgery. I have determined that this danger can be minimized and substantially eliminated so that direct injection into the prosthesis can be made accurately and safely. This is accomplished by not only precisely locating the perimeter of the valve but also and especially important in this procedure of precisely locating the center point thereof so that an accurate perpendicular attitude of the needle relative to the valve can be established to avoid contact with the prothesis wall. The preciseness in location is not possible in present prostheses where location of the valve depends upon palpation nor in those devices using radiopaque material such as disclosed in U.S. Pat. Nos. 3,919,724 and 4,253,201. The valves in these devices are provided with a pocket area filled with a gel mass which includes radiopaque material so that the valve can be identified under X-ray for insertion of the needle. However, it is well known from several studies that significant doses of radiation to the breast tissue may produce dysplastic or tumoral change within the breast and therefore the use of ultrasound for localization of the valve in place of X-ray is preferable since with ultrasound, there is an absence of ionizing radiation to the remaining breast tissue. In the present invention, the improvements for localizing the perimeter and center of the valve, as will later be pointed out, are particularly suitable to ultrasound localization and this is important because in valves with a homogeneous or consistent opaque area, the true dimensions of the valve in an anterior to posterior or front to back dimension cannot be truly appreciated. For this reason, with present devices, it is possible to advance the needle obliquely into the valve while under the impression that one is truly advancing perpendicular to the valve and thus pierce the prosthesis. For those prostheses using double envelopes, there are inherent difficulties in locating the inner envelope with the injection needle without contact and damage to the outer envelope particularly when the envelopes are collapsed to any degree and this is a disadvantage which I have also overcome as will appear.

SUMMARY

One of the important objects of this invention is to provide a double envelope prosthesis for permanent implantation at a selected body location by established surgical procedures that can thereafter, by percutaneous injection through a self-sealing valve, be enlarged or reduced in size or to which steriods, antibiotics and other implant additives can be added or withdrawn without any additional surgical operation and without damage to the walls of the envelopes.

A further object is to provide the self-sealing valve with selected radiopaque indicia designed to delineate precisely the perimeter of such valve and the precise center thereof by means of X-ray and particularly for localization by ultrasound so that the injection needle can be inserted directly into the prosthesis at a predetermined attitude designed to minimize or eliminate the possibility of damage to the prosthesis walls.

Another object herein is to provide a prosthesis as characterized in which the respective injection areas of the outer and inner envelopes are maintained in a secured registering position to assure proper entry of the injection needle into the inner envelope.

In accordance with the present invention, this new prosthesis comprises an outer medical grade elastomer closed envelope having a built-in anterior self-sealing valve and an inner like envelope secured to the posterior of the outer envelope and having an anterior injection receiving area with a self-sealing capability secured in a fixed position of registration to the self-sealing valve. A viscous gel is provided intermediate the envelopes for lubrication to minimize or eliminate the incidence of spontaneous rupture. Selected materials are percutaneously injected into or withdrawn from the inner envelope through the registering injection receiving area on the inner envelope and the valve on the outer envelope with radiopaque indicia associated with the valve to delineate precisely the perimeter of the valve and the precise center thereof for accurate indentification from outside the body by means of X-ray and particularly by ultrasound whereby the needle can be inserted at an accurate perpendicular attitude to valve to eliminate the danger of piercing the envelope walls.

A further object is to provide a prosthesis of the above class with a self-sealing capability only on the valve and a still further object is to provide a prosthesis as characterized using only a single envelope.

The foregoing objects and such further objects as may appear herein, or be hereinafter pointed, together with the advantages of this invention will be more fully discussed and developed in the more detailed description of the accompanying drawings.

BRIEF DESCRIPTION OF THE DRAWINGS

FIG. 3 is a plan view of the prosthesis seen in FIGS. 1 and 2, FIG. 4 is a perspective front view of a second embodiment of an implantable prosthesis similar in appearance from the outside as FIG. 1, FIG. 5 is an enlarged perspective view broken away on the line 5—5 of FIG. 4 to show two interior half shell envelope-like components in relation to the valve assembly, FIG. 6 is a plan view of the prosthesis seen in FIGS. 4 and 5, FIG. 7 is a perspective front view of a third embodiment of an implantable prosthesis in the form of a single envelope and similar in appearance from the outside as in FIGS. 1 and 4, and FIG. 8 is an enlarged cross sectional view of the valve assembly taken on the line 8—8 of FIG. 7.

DESCRIPTION OF THE PREFERRED EMBODIMENTS

Figure 1:
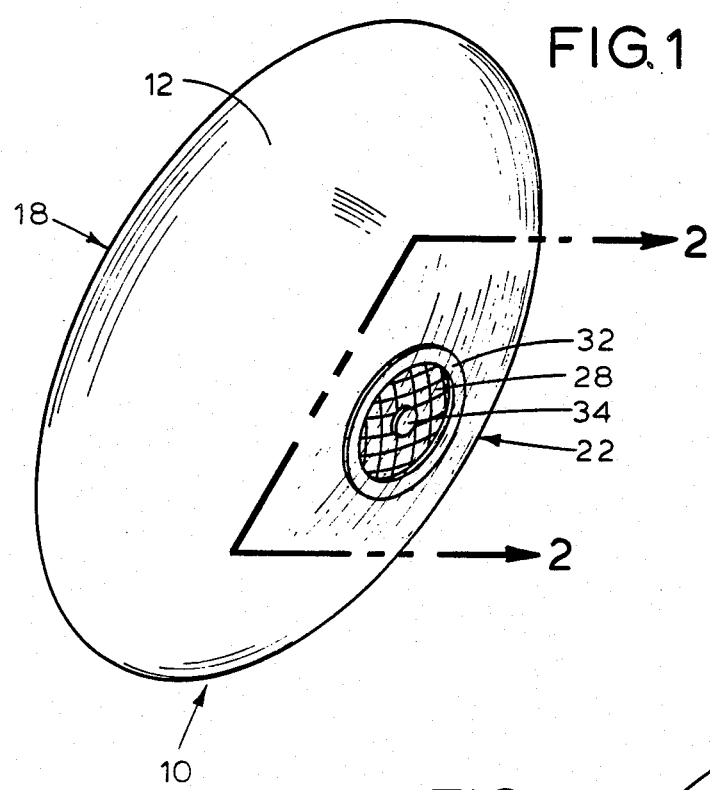
FIG. 1 is a perspective front view of a double envelope or double lumen prosthesis showing the self-sealing radiopaque valve assembly of this invention.

Referring to the drawings, this prosthesis is designated by the numeral 10 and comprises an outer flexible envelope 12, an inner flexible envelope 14 and a valve assembly 16 for defining an injection patch area to receive a hypodermic injection needle (not shown). Both envelopes, 12, 14 are formed of a medical grade silicone elastomer and for purposes of description, define the respective posterior areas 18, 20 and the anterior areas 22, 24.

The valve assembly 16 is bonded to the inside of envelope 12 at the anterior area 22 and includes a relative thin self-sealing valve 26 formed of a layer of 0.007 inch reinforced vulcanized silicone mesh sheeting 28 and a layer of 0.010 inch unvulcanized silicone sheeting 30. This type of valve is commercially available and is designed to close an opening formed by an injection needle when the needle is withdrawn. Similar type valves are disclosed in U.S. Pat. Nos. 3,919,724 and 4,253,201 and no invention is claimed for such valve, per se. As an improvement to valve 26 by valve assembly 16, I have circumscribed the valve 26 with a distinguishing radiopaque band 32 of tantalum or the like to precisely delineate the perimeter of the valve and axially of band 32, I provide the dot or bullseye 34 of similar radiopaque material to precisely identify the center of the valve 26. By this arrangement, both the band 32 and the bullseye 34 can be precisely located by X-ray and particularly by ultrasound where band 32 is clearly visible and the bullseye 34 is shown in the form of an accoustic echo. The advantage of this improvement has been referred to above and will become further apparent in the later description that follows.

The double envelope injectible implant, or double lumen implant at it is also called, has been known and used for some time and as presently used, is made so that the inner envelope or lumen is attached to the outer envelope or lumen only at the posterior area. It is the interior envelope into or from which material is injected or withdrawn so that the injection needle must be accurately placed within the inner envelope for such purpose. Accordingly, if the envelopes are deflated or collapsed in whole or in part relative to the outer envelope, there must be a probing of the needle to locate the anterior area of of the inner envelope which, because it is not secured, may collapse to its posterior area and thus presents considerable danger of the outer envelope being pierced and rendering the prosthesis useless so that it must be surgically removed. I have overcome this disadvantage by the following arrangements.

Figure 2:
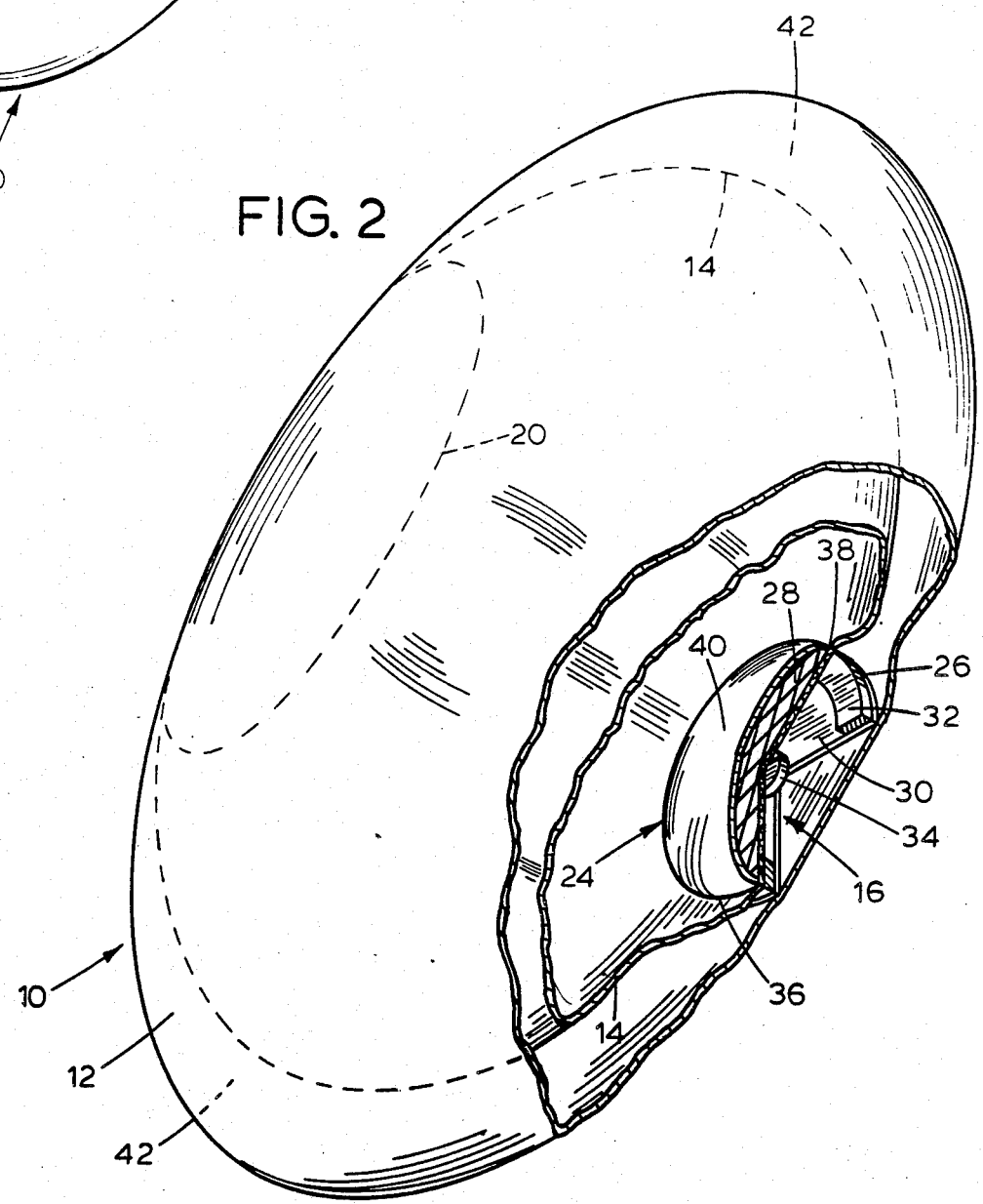
FIG. 2 is an enlarged perspective view broken away on the line 2—2 of FIG. 1 to show the relationship of the inner envelope to the valve assembly.

As seen in FIG. 2, a portion of the inner envelope 14 at the anterior 24 thereof is suitably secured about the perimeter of valve 26 as indicated at 36, 38 to enclose the same and form the pocket 40 which, preferably, has self-sealing material similar to valve 26 bonded to the inner side although this is not required. Pocket 40 serves as the injection area for the inner envelope 14 and is always maintained in proper registration with valve 26. A suitable viscous gel 42 is placed intermediate envelopes 12, 14 for lubrication in a well known manner to minimize or eliminate the incidence of spontaneous rupture.

A second embodiment of this invention, designated generally by the numeral 44, is seen in FIGS. 4, 5 and 6 and includes the outer envelope and valve assembly the same as described for implant 10 so that like parts are given like numerals. Implant 44 differs from implant 10 only in that interiorily of envelope 12 there is provided two opposed half shell shaped members 46, 48 of material the same as envelope 12 secured respectively at the posterior 18 and anterior 22 portions of envelope 12. Such members 46, 48 provide chambers for a gel 42 as shown and in effect form an inner compartment 50 comparable to the interior of the inner envelope 14 for holding selected materials and provides the advantage that an injection needle inserted through valve 26 will be directly in compartment 50 without probing to locate such compartment and without danger to puncturing envelope 12.

A third embodiment 52 is shown in FIGS. 7 and 8 and comprises only a single envelope and valve assembly of the type described for implant 10 so that like parts are given like numerals.

The implant described in the embodiments 10, 44 and 52 is particularly suitable in breast reconstruction and in accordance with established surgical procedures can be implanted immediately after the initial operation to remove diseased tissue. It is recommended that insertion of this implant be through an inframmary approach so that the implant is placed not only behind the pectoral but also the serratus anterior muscles. The initial filling of the implant with appropriate fluids may be accomplished by a hypodermic needle through valve 26. However, since access to the implant is available for filling while the original incision is still open, I recommend and prefer that the implant be provided with a filling valve for catheter filling as disclosed in U.S. Pat. No. 4,178,643 but with the further recommendation that such filling valve be moved from its disclosed posterior location to a point at the periphery of the implant approximately midway between the posterior and anterior apexes and thereby made more readily accessible through the original incision which can then be kept at a smaller size for both insertion of the implant and initial filling than is required if the filling valve is located posteriorly.

Postoperatively, the implant may require additions or withdrawals of fluids or other additives as indicated above and for this purpose, valve assembly 16 is designed to effectively and efficiently permit such procedures by use of a hypodermic needle through valve 26 without the necessity for additional surgical procedures which are preferably avoided whenever possible and without danger of damage to the implant envelope or envelopes. In this regard, the radiopaque band 32 and the radiopaque bullseye 34 can be precisely delineated not only by X-ray but more particularly by ultrasound which is preferable to X-ray since it does not produce ionizing radiation to the remaining breast tissue that can have deleterious affects as pointed out earlier. Such precise location of band 32 and bullseye 34 at the center of valve 26 permits the hypodermic needle to be oriented perpendicularly to the valve 26 which is the most efficient attitude for injection without danger of being angularly oriented to the envelope wall. The ability of the valve assembly 16 to permit the precise correct attitude of the needle is not presently possible in other prostheses using radiopaque material since in such devices, as referred to above, the radiopaque material is only present in a fluid mass of the same consistency with no change in texture from one side to the other so that precise demarcation of the extremity of the valve and particularly the precise center thereof is difficult by X-ray and particularly difficult by ultrasound which is clearly superior to X-ray in terms of decreased radiation doseage to the patient. A further advantage to the use of ultrasound whenever possible for localization of the valve for the purposes described is the fact that ultrasound allows accurate depth localization of the needle that is not easily available with X-ray and such depth localization is important to prevent inadvertent puncture of the posterior wall of the prosthetic device with subsequent leakage of fluid.

By being able to establish the precise point of the bullseye 34, a suitable mark can be placed on the skin so that the hypodermic needle can be inserted perpendicularly to valve 26. With the double envelope embodiment 10 (FIG. 2), the needle will register with pocket 40 for injection into envelope 12; with embodiment 44 (FIG. 5), the needle will be within compartment 50 after penetrating valve 26, and in embodiment 52 (FIG. 7), the needle will be centrally within envelope 12. It is thus apparent that by use of valve assembly 16 as described, the percutaneous injection of the implant can be made accurately and safely without damage to the implant. Accordingly, in view of the foregoing, it is thought a full understanding of the construction and operation of this invention will be had and the advantages of the same will be appreciated.

I claim:

1. A prosthesis for permanent implantation in a body cavity, comprising:
    a closed flexible envelope of medical grade elastomer for containing selected materials defining an anterior area for orientation towards the outer skin surface and an opposed posterior area,
    a self-sealing valve fixedly disposed on the inner surface of said anterior area and adapted to be pierced by a hypodermic needle after implantation of said prosthesis,
    a band of radiopaque material circumscribing said valve so that the precise perimeter of said valve can be delineated by means of X-ray and by means of ultrasound,
    a pair of opposed half-shell shaped members of medical grade elastomer disposed within said envelope,
    each one of said members secured at one end to the posterior area of said envelope and secured at its other end to a portion of the perimeter of said valve to form a compartment in said envelope in registration with said valve defining the material receiving area of said envelope and further forming respective chambers intermediate said respective members and said envelope, and
    a lubricating gel disposed in each chamber.

2. A prosthesis as defined in claim 1 including a bullseye-like dot of radiopaque material disposed on said anterior area axially of said band so that the precise center of said valve can be delineated by means of X-ray and by means of ultrasound.

3. A prosthesis for permanent implantation in a body cavity, comprising:
    a closed flexible envelope of medical grade elastomer for containing selected materials defining an anterior area for orientation towards the outer skin surface and an opposed posterior area,
    a self-sealing valve fixedly disposed on the inner surface of said anterior area and adapted to be pierced by a hypodermic needle after implantation of said prosthesis,
    a bullseye-like dot of radiopaque material disposed on said anterior area axially of said valve so that the precise center of said valve can be delineated by means of X-ray fluoroscopy and by means of ultrasound,
    a pair of opposed half-shell shaped members of medical grade elastomer disposed within said envelope,
    each one of said members secured at one end to the posterior area of said envelope and secured at its other end to a portion of the perimeter of said valve to form a compartment in said envelope in registration with said valve defining the material receiving area of said envelope and further forming respective chambers intermediate said respective members and said envelope, and
    a lubricating gel disposed in each chamber.

4. A prosthesis for permanent implantation in a body cavity, comprising:
    a closed flexible envelope of medical grade elastomer for containing selected materials defining an anterior area for orientation towards the outer skin surface and an opposed posterior area,
    a self-sealing valve fixedly disposed on the inner surface of said anterior area and adapted to be pierced by a hypodermic needle after implantation of said prosthesis,
    a pair of opposed half-shell shaped members of medical grade elastomer disposed within said envelope,
    each one of said members secured at one end to the posterior area of said envelope and secured at its other end to a portion of the perimeter of said valve to form a compartment in said envelope in registration with said valve defining the material receiving area of said envelope and further dorming respective chambers intermediate said respective members and said envelope, and
    a lubricating gel disposed in each chamber.

5. A breast prosthesis for permanent implantation in a body breast cavity, comprising:
    a first closed flexible envelope of medical grade elastomer defining an anterior area for orientation towards the outer skin surface and an opposed posterior area,
    a self-sealing valve fixedly disposed on the inner surface of said anterior area and adapted to be pierced by a hypodermic needle after implantation of said prosthesis,
    a second closed flexible envelope of medical grade elastomer disposed within said first envelope,
    a portion of said second envelope bonded to the posterior area of said first envelope and the opposed portion of said second envelope bonded to the perimeter of said valve to provide a pocket member in juxtaposition with said valve and in permanent registration therewith so that when a hypodermic needle is inserted through said valve, it can enter said second envelope through said pocket member, and
    a band of radiopaque material circumscribing said valve so that the precise perimeter of said valve can be delineated by means of X-ray fluoroscopy and by means of ultrasound.

6. A prosthesis as defined in claim 5 including a lubricating gel intermediate said first and second envelopes.

7. A prosthesis as defined in claim 5 including a bullseye-like dot of radiopaque material disposed on said anterior area axially of said band so that the precise center of said valve can be delineated by means of X-ray fluoroscopy and by means of ultrasound.

8. A prosthesis as defined in claim 7 including a lubricating gel intermediate said first and second envelopes.

9. A breast prosthesis for permanent implantation in a body breast cavity, comprising:

a first closed flexible envelope of medical grade elastomer defining an anterior area for orientation towards the outer skin surface and an opposed posterior area, a self-sealing valve fixedly disposed on the inner surface of said anterior area and adapted to be pierced by a hypodermic needle after implantation of said prosthesis, a second closed flexible envelope of medical grade elastomer disposed within said first envelope, a portion of said second envelope bonded to the posterior area of said first envelope and the opposed portion of said second envelope bonded to the perimeter of said valve to provide a pocket member in juxtaposition with said valve and in permanent registration therewith so that when a hypodermic needle is inserted through said valve, it can enter said second envelope through said pocket member, and a bullseye-like dot of radiopaque material disposed on said anterior area axially of said valve so that the precise center of said valve can be delineated by means of X-ray fluoroscopy and by means of ultrasound.

10. A prosthesis as defined in claim 9 including a lubricating gel intermediate said first and second envelopes.

* * * * *